United States Patent [19]
Rubin

[11] Patent Number: 5,797,885
[45] Date of Patent: Aug. 25, 1998

[54] APPARATUS AND METHOD FOR RECAPPING SYRINGE NEEDLES

[76] Inventor: Gregory R. Rubin, 24704 Calle Conejo, Calabasas, Calif. 91302

[21] Appl. No.: 901,435

[22] Filed: Jul. 28, 1997

[51] Int. Cl.⁶ .................................................. A61M 5/32
[52] U.S. Cl. .................................. 604/192; 604/263
[58] Field of Search ................................ 604/263, 187, 604/192, 110; 206/365, 366

[56] References Cited

U.S. PATENT DOCUMENTS

| | | | |
|---|---|---|---|
| 4,380,292 | 4/1983 | Cramer | 604/192 X |
| 4,629,453 | 12/1986 | Cooper | 604/192 |
| 4,892,525 | 1/1990 | Hermann, Jr. et al. | 604/192 |
| 5,183,469 | 2/1993 | Capaccio | 604/192 |
| 5,209,738 | 5/1993 | Bruno | 604/263 X |
| 5,230,428 | 7/1993 | McShane | 604/192 X |
| 5,325,965 | 7/1994 | Kelley | 206/366 |
| 5,334,151 | 8/1994 | Santilli | 206/365 |
| 5,347,078 | 9/1994 | Eckels | 206/365 X |

*Primary Examiner*—John D. Yasko
*Attorney, Agent, or Firm*—Robert J. Schaap

[57] ABSTRACT

An apparatus and a method for recapping of syringe needles while substantially reducing the risk of injury to the user during the recapping thereof. In one embodiment, the apparatus comprises a cap holder with a base and a weight distribution such that a cap retained in the cap holder is always oriented in an upright position with the upper end thereof being opened. In this way the user of the syringe, can release a needle from the syringe with one hand, and drop the needle into the syringe cap where a cover may thereupon be placed over the open end of the cap. Thereafter, the needle and cap-cover arrangement can be discarded. In another embodiment, a needle retaining element, such as a piece of gauze, foam or the like can be located in the needle cap such that when the needle is inserted into the gauze or foam, it will be at least partially grasped to thereby hold the needle while the user releases the needle from the syringe.

15 Claims, 1 Drawing Sheet

U.S. Patent  Aug. 25, 1998  5,797,885
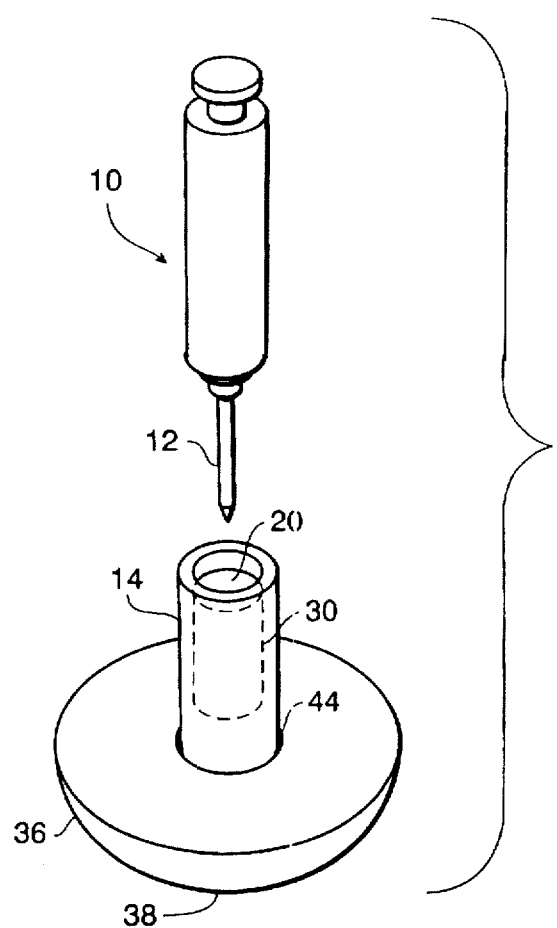
FIG. 1
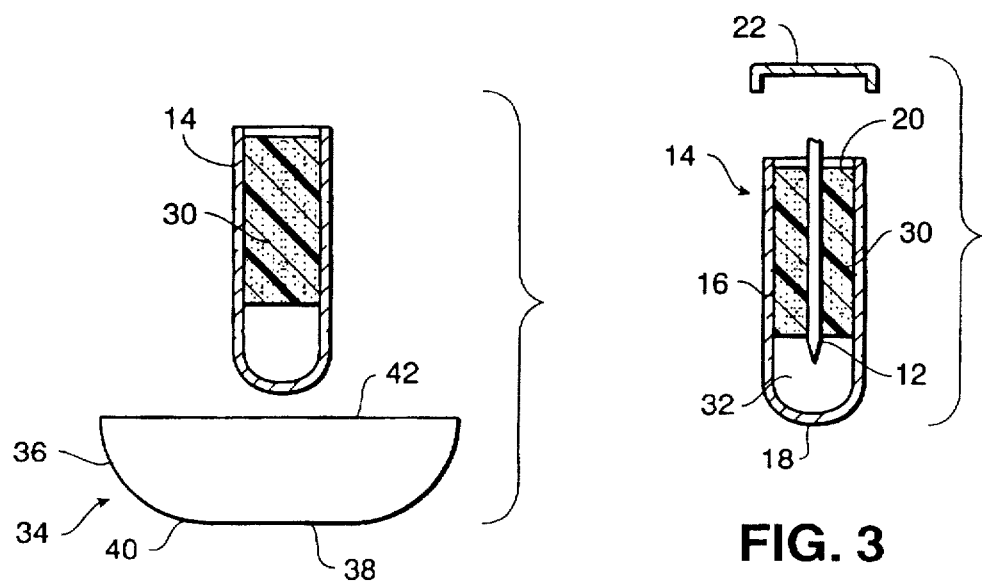
FIG. 2
FIG. 3

APPARATUS AND METHOD FOR RECAPPING SYRINGE NEEDLES

BACKGROUND OF THE INVENTION

1. Field of the Invention

This invention relates in general and certain new and useful improvements in an apparatus and method for disposing of syringe needles, and more particularly, to an apparatus and method of the type stated which allows the disposing of such syringe needles with substantially reduced risk of injury to the user thereof.

2. Brief Description of the Related Art

It is a recommended practice for most health professionals, such as physicians, dentists, nurses and their assistants to recap a used syringe needle after using same on is a patient. Usually, conventional syringe needles are provided in disposable cylindrically shaped tubular containers having open ends, or so-called "caps". These caps are usually provided with a removable cover or lid, as well.

When it is desired to use a syringe needle, the user, such as the health professional, removes the needle from the cap, inserts the same into the syringe and will use the syringe and needle arrangement to either inject a medicament into a patient or remove a sample from a patient. The syringe needles are almost always sterilized when received and thus, if the health professional should inadvertently scratch or puncture his or her skin, there is generally no serious risk.

However, with the increased risk of the HIV virus and other contagious micro-organisms, the puncturing of a user's skin with a used needle can become a matter of serious concern.

It is presently a recommended practice for all health professionals to recap these needles after they are used. In this way, there is less risk of damage to someone emptying trash containing used needles and there is even a reduced risk to the user in handling the used needle. However, the task of recapping a used needle, itself, presents a health risk to a health professional. Many times, the health professional in an attempt to introduce the used needle into the small open end of the needle cap often misses the opening and inadvertently scratches or punctures his or her skin, thereby creating a potentially serious health concern from contracting a highly contagious and oftentimes, a potentially fatal disease. Even the emotional concern over whether or not the health professional has even contracted a contagious disease is a matter of serious concern.

There is presently no effective means for enabling a health professional to insert the used needle back into the needle cap without the attendant risk of injuring the user. However, there is still a need to recap used needles and consequently, there is a concomitant need to provide some means by which a user can recap a needle with one hand so that the possibility of injury to the user is substantially reduced. The present invention provides that apparatus necessary for recapping a used needle without the attendance of serious risk of injury to the user.

OBJECTS OF THE INVENTION

It is, therefore, one of the primary objects of the present invention to provide a needle cap constructed so that a user can release a needle from a syringe with one hand and introduce a used needle into the needle cap without the attendant injury of puncturing or scratching the user.

It is another object of the present invention to provide a needle cap of the type stated in which a retaining element can be disposed tightly within the needle cap to frictional retain and hold a needle when the latter is introduced therein.

It is an additional object of the present invention to provide an apparatus for allowing a needle cap to always assume an upper right position with its open end being upwardly disposed so that a user can easily and readily deposit a needle from a syringe into the needle cap with one hand.

It is an additional object of the present invention to provide an apparatus of the type stated which allows for the dropping of a used needle into a needle cap and also recovering the needle cap with one hand.

It is another salient object of the present invention to provide a needle cap arrangement of the type stated which can be constructed at a low cost and which is highly effective in use.

With the above and other objects in view, my invention resides in the novel features of form, construction, arrangement, and combination of parts as presently described and pointed out in the claims.

SUMMARY OF THE INVENTION

The present invention relates an apparatus and method for allowing for the recapping of used syringe needles. In one of the preferred embodiments, a conventional needle cap is fitted with a needle retaining member, such as a piece of gauze, or foam, or the like, which can frictionally engage and physically hold a needle with a reasonable degree of grasping force when a needle connected to a syringe is pushed into the retaining member. After the needle has been pushed into the retaining member, the health professional can release the needle from the syringe effectively with one hand and thereby reduce the risk of injury to the health professional.

As previously described, most injury to health professionals arise from used needles when two hands are used to remove the needle from the syringe such that the user with the syringe in one hand inadvertently scratches or punctures or otherwise breaks the skin of the other hand of the user. In the present invention, after the needle is held in the retaining member, the cover can then be placed over the needle cap and the assembly thereof discarded without further risk to waste attendants, or the health users or others.

In another embodiment of the invention, there is provided a needle cap holder which is shaped and weighted such that a needle cap retained by the holder is always located in an upright position, such that the open end of the needle cap is upwardly disposed. In this way, a user of a syringe and needle, with one hand, can release the needle from the syringe and allow the same to drop into the needle cap. The cap can thereupon be covered with the cover and again discarded.

In a more preferred embodiment, a needle cap containing the gauze is used with the aforesaid needle cap holder having a base to orient the holder in an upright position. In this way, there is an even further reduction in risk of injury to the user.

The present invention thereby fulfills all of these and other objects and advantages in the provision of a unique needle cap arrangement in which a used needle can be deposited in a needle cap with substantially reduced risk of injury to the user. The present invention thereby fulfills the above and other objects with the apparatus and method described in the following detailed description and illustrated in the accompanying drawings. However, it should be understood that this apparatus and the associated method is

3 only set forth for purposes of illustrating the general principles of the invention and is not to be taken in a limiting sense.

BRIEF DESCRIPTION OF THE DRAWINGS

Having thus described the invention in general terms, reference will now be made to the accompanying drawings in which:

FIG. 1 is a perspective view of an assembly for allowing the re-introduction of a used needle into a needle cap in accordance with the present invention;

FIG. 2 is a side elevational view, partially broken away and in section, and showing a needle cap holder along with a needle cap and needle retaining member therein; and FIG. 3 is an enlarged vertical sectional view of a needle retained in a needle retaining member in a needle cap.

DETAILED DESCRIPTION OF A PREFERRED EMBODIMENT

Referring now in more detail and by reference characters to the drawings, which illustrate preferred embodiments of the present invention, A designates a needle cap assembly which allows for the re-introduction of a used needle into a needle cap. In the embodiment as illustrated in FIG. 1, a lower portion of a conventional syringe 10 is shown and which holds a releasable syringe needle 12.

The needle cap assembly A comprises a conventional needle cap 14, such as the cap in which the syringe needle 12 was initially supplied. Generally, the conventional needle cap comprises a cylindrically shaped sidewall 16 and an enclosing bottom wall 18 along with an open end 20 with the latter being designed to provide access to a needle stored therein. A removable cover or so-called "lid" 22 is often provided with the needle cap 14. The needle cap is preferably made of a transparent plastic material, but which is of a sufficiently thick wall construction, such that the point of the needle cannot penetrate the needle cap.

In accordance with one embodiment of the invention, the needle cap is provided with a needle retaining member 30 in an interior chamber 32 of the needle cap. This retaining member may adopt the form of any material which can receive a needle pushed therein, as for example, a piece of foam material or gauze material or the like. The retaining member 30 is snugly fitted within the chamber 32 so as to be retentively held in the chamber 32. However, it is also sufficiently yieldable and puncturable to receive a used needle when the point is pushed through the material forming the retaining member 30. As this occurs, the retaining member will frictional engage and hold the needle 12 when the latter is released from the syringe.

The needle cap retaining member 30 is formed of a material which will frictionally engage and retentively hold the needle when the latter is inserted into the retaining member. Only a slight amount of manual force is required to push the needle into the retaining member when the latter is connected to a syringe. After the needle is pushed into the retaining member, it is released from the syringe, and a cap can then be placed over the needle cover. The retaining member 30 is preferably formed of a gauze-like material or otherwise, it may be formed of a resilient foam, such as a polyethylene foam or otherwise a polystyrene foam.

The needle cap of the invention may be used with the needle cap retaining member and the lid 22. Thus, an attendant can hold the needle cap in one hand, and with the other hand, guide the syringe needle directly into the retaining member 30 through the open end 20 of the needle cap. After the latter is released, the lid is then conventionally placed over the open end 20, and the entire cap can then be discarded.

In a preferred embodiment of the present invention, the needle cap 14 is secured to a base 34 with a size and shape so that it will always remain in an upright position. For this purpose, the base 34 is provided with somewhat of an arcuately shaped side wall 36, and relatively flat bottom wall 38, all as best shown in FIGS. 1 and 2 of the drawings. The arcuate side wall 36 merges into the base wall or bottom wall 38 through somewhat of an arcuate ridge or lower edge 40, also as best shown in FIG. 2 of the drawings. The base 34 is also provided with a relatively flat upper surface 42, in turn, provided with a cylindrically shaped groove or recess 44 for receiving the lower end of the needle cap 14.

When it is desired to use the needle cap 14 in the base 34, the latter is removably inserted into the opening 44 where the needle cap will be retained in a generally vertical upright position. The base is constructed so that, even if it is tipped to one side or another, it will always return to its initially stable upright position, as shown in FIG. 2. The base is properly weighted so that it will always assume this upright position. Moreover, the arcuate side wall 36, along with the arcuate ridge 40 and the relatively flat bottom wall 38, also aid in achieving this up righting of the base to the position as shown.

In accordance with the construction as shown in FIGS. 1 and 2, when the needle cap 14 is used in the base 34, the needle can be secured to the syringe with one hand, and literally removed from the syringe with one hand. For this purpose, the lower end of the syringe is inserted through the open upper end 20 of the needle cap and maneuvered into position to engage the upper end of the needle. The syringe is then locked to the needle. After the needle has been used, the attendant, such as the medical personnel, can then re-introduce the needle back into the needle cap 14 while the attendant merely engages the syringe 10. The needle is then pushed into the gauze or other retaining member 30. Thereafter, the needle is released from the syringe and the lid 22 is disposed over the open upper end 20, so that the cap and lid can be disposed of with the needle captured therein.

It can also be observed with the present invention that when the needle cap 14 is used with the base 34, it is not absolutely necessary to use a retaining member 30 within the needle cap. However, the retaining member 30 is desirable since it will physically engage and hold the needle within the cap 14.

The base 34 may preferably be formed of a wooden material or a plastic material or other structural type material, in a relatively low cost manner. Thus, and in this respect, if desired, the base 34 could be disposable. However, the base 34 is usually retained as a permanent item, where the needle cap and needle are discarded after each use.

Thus, there has been illustrated and described a unique and novel apparatus and method for recapping a syringe needle, and which thereby fulfills all of the objects and advantages which have been sought therefor. It should be understood that many changes, modifications, variations and other uses and applications will become apparent to those skilled in the art after considering this disclosure and the accompanying drawings. Therefore, any and all such changes, modifications, variations, and other uses and applications which do not depart from the spirit and scope of the invention are deemed to be covered by the invention.

Having thus described the invention, what I desire to claim and secure by letters patent is:

1. A novel syringe cap assembly for receiving and retaining a used syringe needle, and retentively holding same therein, said novel needle cap assembly comprising:

a) a needle cap having a cylindrically shaped side wall and a bottom wall and an end wall extending across one end of the side wall and an open end opposite the end wall, said cylindrically shaped side wall having an axial extent from the open end to the end wall;

b) a needle cap retaining member frictionally held within an interior chamber of said needle cap, said retaining member being formed of a material which will receive penetration of a needle therein, and frictionally and retentively hold the same and yet allow a pulling of the needle from the retaining member if required, said retaining member having an axial length extending for a greater portion of the overall axial extent of the needle cap side wall to enable relatively tight gripping force to be applied to the syringe needle for a substantial portion of its length; and c) a lid capable of being disposed over the open end of said needle cap after the syringe needle has been inserted into the retaining member.

2. The novel needle cap assembly of claim 1 further characterized in that the retaining member is formed of a flexible and yield able foam material.

3. The novel needle cap assembly of claim 1 further characterized in that the enclosing end wall is a bottom wall, and has an upwardly opening end.

4. The novel needle cap assembly of claim 1 further characterized in that the retaining member is formed of a gauze material.

5. The needle cap retaining assembly of claim 1 further characterized in that said enclosing side wall is cylindrically shaped.

6. The novel needle cap assembly of claim 5 further characterized in that said needle cap is generally transparent so that a user can view the insertion of the needle into the retaining member.

7. A novel syringe needle retaining assembly which allows for a safe recapping of a syringe needle after use thereof, said needle assembly comprising:

a) a base having a configuration and weight distribution such that an upper surface thereof will always assume a generally upright position when the base is disposed on a relatively flat and relatively horizontal surface;

b) means in said base for retaining a needle cap; and c) a needle cap secured to the upper surface of said base at said means for retaining the needle cap;

d) said base being shaped and weighted so that the needle cap retained therein will always automatically shift to and remain in a generally upright position thereon so that an open end of a needle cap is generally upwardly disposed, whereby an attendant may introduce a used needle through the open end of the needle cap and into the needle cap and allow depositing of the needle cap therein with manipulation requiring only a single hand.

8. The needle cap assembly of claim 7 further characterized in that a retaining member is disposed within the needle cap for frictionally engaging and retentively holding the syringe needle when the latter is pushed thereinto.

9. The needle cap retaining assembly of claim 7 further characterized in that the retaining member is formed of a flexible and yieldable foam material.

10. The needle cap retaining assembly of claim 7 further characterized in that the enclosing end wall is a bottom wall, and has an upwardly opening end.

11. The needle cap retaining assembly of claim 7 further characterized in that the retaining member has a length which extends for a greater portion of the overall length of the needle cap to enable a relatively tight gripping force to be applied to the syringe needle.

12. The needle cap retaining assembly of claim 7 further characterized in that said enclosing side wall is cylindrically shaped.

13. The needle cap retaining assembly of claim 7 further characterized in that said needle cap is generally transparent so that a user can view the insertion of the needle into the retaining member.

14. A method for recapping of a used syringe needle while reducing risk of penetration or a scratching of the hands of a user, said method comprising:

a) introducing a used syringe needle into a flexible retaining member disposed within a needle cap and where the retaining member extends for a greater portion of the length of the needle cap to enable a relatively tight gripping of the syringe needle, such that the needle cap is pushed into the retaining member while on a syringe and thereafter released from the syringe;

b) inserting a lid over the open end of the needle cap after the used syringe needle has been inserted therein; and c) discarding the used syringe needle enclosed within the needle cap and lid.

15. The method of claim 14 further characterized in that the method comprises inserting the needle cap into a holder which automatically assumes a generally upright position regardless of previous orientation so that the needle cap will also have an open end generally upwardly disposed, and which thereby allows for one hand recapping of the used syringe needle.

* * * * *